United States Patent
Nishio et al.

(10) Patent No.: US 7,686,932 B2
(45) Date of Patent: Mar. 30, 2010

(54) GAS SENSOR

(75) Inventors: Hisaharu Nishio, Toukai (JP); Takashi Nakao, Kasugai (JP); Kazuhiro Kohzaki, Komaki (JP); Keiichi Adachi, Kani (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1010 days.

(21) Appl. No.: 11/235,201

(22) Filed: Sep. 27, 2005

(65) Prior Publication Data

US 2006/0065541 A1 Mar. 30, 2006

(30) Foreign Application Priority Data

Sep. 28, 2004 (JP) ................ P.2004-282467

(51) Int. Cl.
*G01N 27/407* (2006.01)
(52) U.S. Cl. ...................... 204/428; 204/424
(58) Field of Classification Search ......... 204/421–429; 205/781, 783.5, 784.5
See application file for complete search history.

(56) References Cited

U.S. PATENT DOCUMENTS

| | | | | |
|---|---|---|---|---|
| 4,065,372 A | * | 12/1977 | Hacker et al. | ............... 204/428 |
| 5,762,771 A | | 6/1998 | Yamada et al. | |
| 6,214,186 B1 | * | 4/2001 | Watanabe et al. | .......... 204/428 |
| 6,303,013 B1 | | 10/2001 | Watanabe et al. | |
| 2002/0144538 A1 | | 10/2002 | Yamada et al. | |

FOREIGN PATENT DOCUMENTS

| | | |
|---|---|---|
| EP | 1391724 A1 | 2/2004 |
| JP | 61-502702 A | 11/1986 |
| JP | 62186061 U | 11/1987 |
| JP | 5149914 A | 6/1993 |
| JP | 2000-88795 A | 3/2000 |
| JP | 2000-180401 A | 6/2000 |
| JP | 2000-258384 A | 9/2000 |

OTHER PUBLICATIONS

Japanese Office Action dated May 12, 2009.

* cited by examiner

*Primary Examiner*—Nam X Nguyen
*Assistant Examiner*—Kourtney R Salzman
(74) *Attorney, Agent, or Firm*—Sughrue Mion, PLLC

(57) ABSTRACT

A gas sensor including: a cylindrical metal shell; a detection element having a detection portion provided on a front end side thereof, the detection element being fixed inside the metal shell while the detection portion of the detection element protrudes from a front end side of the metal shell; and an element protection cap having ventholes, the element protection cap being fixed to the metal shell so that the detection portion of the detection element is covered with the element protection cap. A crimping cylindrical portion is provided which extends to a front end side of the metal shell. A protrusion portion of the element protection cap which abuts a metal ring packing is provided with concave and convex portions outward along an outer circumferential direction. As such, the metal ring packing is deformed so as to be interlocked with the concave and convex portions when the crimping cylindrical portion is compressively deformed.

10 Claims, 11 Drawing Sheets

GAS SENSOR

BACKGROUND OF THE INVENTION

1. Field the Invention

The present invention relates to a gas sensor for measuring oxygen concentration, air-fuel ratio state, NOx concentration, etc., in exhaust gas of an internal combustion engine.

2. Description of the Related Art

A gas sensor employing a detection element made of a solid electrolyte such as zirconia is known as a gas sensor for detecting oxygen concentration, etc., in a gas to be measured such as exhaust gas. A bottomed cylinder-shaped (cup-shaped or test tube-shaped) element having a closed front end, a rod-shaped (plate-shaped) element made of a laminate of sheets, etc., can be used as the detection element. Any of these detection elements (hereinafter also referred to as an "element") has a detection portion provided at its front end and which is brought into contact with the gas to be measured. The element is formed so that the detection portion is exposed to the gas to be measured. For example, in an oxygen sensor having a bottomed cylinder-shaped detection element made of an oxygen ion conductor, the detection element is positioned and fixed into a cylindrical metal shell such that the front end side of the element protrudes from a front end side of the metal shell. The metal shell (hereinafter also referred to as "shell") is attached to an exhaust pipe of an internal combustion engine in such manner that the shell is screwed into the exhaust pipe, for example, by a male thread formed on the outer circumferential-surface of the shell. The shell is arranged such that the front end of the detection element protrudes into the exhaust pipe. Thus, while an electrode layer (measurement electrode layer) formed on the outer circumferential surface (outer surface) of the detection element contacts the exhaust gas, an electrode layer (reference electrode layer) formed on the inner circumferential surface (inner surface) of the detection element contacts a reference oxygen-containing gas (e.g., atmospheric air) to thereby generate an electromotive force (electric potential difference) between the two electrodes in accordance with the oxygen concentration difference between the inner and outer circumferential surfaces of the element. A signal based on the electromotive force is output to a control circuit so that the oxygen concentration is detected and the air-field ratio is controlled.

This type gas sensor is attached to the exhaust gas pipe so that the front end side of the element protrudes into the exhaust gas pipe. Upon attachment, there is a possibility that the element will crack because of collision of the front end side of the element with the exhaust gas pipe. Because the front end of the element is exposed to a severe atmosphere or condition such as high-temperature exhaust gas or a heat cycle, it is necessary to protect the detection element of a solid electrolyte or the electrode layer formed on the front surface of the detection element. Therefore, a metal element protection cap (also called "protection pipe", "protector" or "element cover") provided with an adequate number of ventilation through-holes (ventholes) is generally attached to the front end side of the element. As a result, the exhaust gas can pass through the ventholes so that the exhaust gas contacts the measurement electrode layer on the outer circumferential surface of the element.

This type element protection cap (hereinafter also referred to as a "cap") is shaped like a cup, etc., so that the front end side of the element protruding from the front end side of the metal shell is covered with the cap. Typical means for fixing the element protection cap to the metal shell include a welding structure in which laser welding or resistance welding is applied after the cap is fitted to the front end side of the shell, or a fixing means which uses crimping (Japanese Patent Publication No. 15221/1993). The crimping is performed as follows. First, a protrusion portion such as a flange protruding to the outside (outwards) is provided on the outer circumference of an open end in the rear end side of the element protection cap. On the other hand, a front-end-facing end surface is provided in a front end region of the metal shell and a crimping cylindrical portion is provided in the outer circumference of the front-end-facing end surface so that an end region including the flange can be enclosed in the crimping cylindrical portion when the element protection cap is inserted in the metal shell. In a condition such that the end region is disposed in the cylindrical portion, the cylindrical portion is compressively deformed in an axial direction while being bent inward. The compressive deformation of the cylindrical portion, that is, crimping, allows the flange to be intensively pressed against the front-end-facing end surface side of the metal shell to thereby fix the element protection cap to the metal shell. In the fixing structure which uses crimping, a technique for interposing a metal ring (packing) in order to improve the fixing force is known (Japanese Utility Model Laid-Open No. 186061/1987).

3. Problems to be Solved by the Invention

In the fixing structure of the element protection cap (protection pipe) described in Japanese Patent Publication No. 15221/1993, a problem of rattling or moving may occur in the element protection cap. This is because a turn-back edge of the compressively deformed crimping portion is loosened by high-temperature exhaust gas or a repeated heat cycle so that the element protection cap is completely fixed. Particularly in this structure, reliability of the fixing force is problematic because the element protection cap is apt to be loosened around the axis of the male thread of the shell. It is considered that the cause of loosening in the fixing structure using crimping is the presence of residual stress generated in respective parts at the time of crimping, the buckling of the compressively deformed portion, etc., in addition to the heat cycle.

In the fixing structure of the element protection cap (protector) described in Japanese Utility Model Laid-Open No. 186061/1987, an increase in fixing force is attained by interposing a the metal ring packing, but there is still a risk that the crimping portion may be loosened.

SUMMARY OF THE INVENTION

The invention has been accomplished in consideration of the above-described problems of the prior art. Accordingly, an object of the invention is to provide a structure for fixing an element protection cap to a shell by crimping, that is, by compressively deforming a crimping cylindrical portion of the shell, with such strong fixing force that the crimping portion can be effectively prevented from becoming loosened.

(1) The foregoing object of the invention has been achieved by providing, in a first aspect, a gas sensor including: a cylindrical metal shell; a detection element having a detection portion provided on a front end side thereof the detection element being fixed inside the metal shell while the detection portion of the detection element protrudes from a front end side of the metal shell; and an element protection cap having ventholes, the element protection cap being fixed to the metal shell so that the detection portion of the detection element is covered with the element protection cap; the metal shell including an annular front-end-facing end surface provided in a front end region of the metal shell, and a crimping cylindrical portion extending to the front end side on an outer circumference of the front-end-facing end surface; the element protection cap including a protrusion portion which extends outward from a rear end side of the element protection cap and is received in the crimping cylindrical portion, the protrusion portion of the element protection cap being disposed in the crimping cylindrical portion while a metal ring packing is disposed so as to abut a front end facing surface of the protrusion portion, the crimping cylindrical portion being compressively deformed toward the front-end-facing end surface while being bent inward to cover the metal ring packing so that the protrusion portion of the element protection cap is pressed against the front-end-facing end surface through the metal ring packing thereby fixing the element protection cap to the metal shell; wherein: the protrusion portion of the element protection cap on which the metal ring packing abuts includes concave and convex portions provided outward along an outer circumferential direction, so that the metal ring packing is deformed and thereby interlocked with the concave and convex portions when the crimping cylindrical portion is compressively deformed.

According to the embodiment described in (1) above, a typical example in which the protrusion portion at the open end on the rear end side of the element protection cap includes concave and convex portions provided outward along the outer circumferential direction includes a shape of outer teeth formed from regions where the protrusion portion is present and regions where the protrusion portion is not present. Also in the case where the shape of outer teeth is formed, the outer teeth (convex portions) may be arranged along the outer circumference of an annular flange from which the protrusion portion is formed. The outer teeth may be arranged over the entire outer circumference of the open end (base end) of the element protection cap or notched teeth may be furnished so that one tooth (convex portion) or a plurality of teeth (convex portions) are provided. In the case where a plurality of teeth (convex portions) are provided, the teeth may be arranged at regular angular intervals or at irregular angular intervals in the circumferential direction. Furthermore, the metal ring packing for use in the invention is not limited to an endless ring. For example, an end ring prepared such that a single wire is rounded in the form of a ring may serve as the metal ring packing. In addition, the metal ring packing is preferably formed of a metal having a hardness lower than that of the material of the metal shell or the element protection cap.

According to the embodiment described in (1) above, because the metal ring packing is deformed so as to be relatively interlocked with the concave and convex portions, the element protection cap is more firmly fixed to the metal shell as compared to a background-art fixing structure using crimping incapable of deforming the metal ring packing in this manner. Moreover, by means of the concave and convex portions, both a pressure bonding portion between the front-end-facing end surface of the shell and the protrusion portion of the cap, and a pressure bonding portion between the metal ring packing and the compressively deformed crimping cylindrical portion are provided, such that the regions having the convex portions are pressure-bonded so as to bear a relatively high pressure in the circumferential direction. Because regions bearing a relatively high pressure are thus obtained, the fixing force of the cap can be increased. Accordingly, the element protection cap can be fixed by a high fixing force, so that the element protection cap can be restrained from being rattled or moved.

(2) In a preferred embodiment, a gas sensor according to (1) above is provided, wherein: a protrusion portion of an element protection cap formed as an annular flange is provided in place of the protrusion portion of the element protection cap including concave and convex portions provided outward along the outer circumferential direction; and a front end facing surface of the flange is provided with concave and convex portions along a circumferential direction so that the metal ring packing is deformed and thereby interlocked with the concave and convex portions.

In the gas sensor according to (1) above, metal ring packing to be interlocked with the concave and convex portions of the protrusion portion of the element protection cap is preferably deformed from the surface (front end facing surface) of the protrusion portion on the side where the metal ring packing abuts, into each concave portion between adjacent convex portions for forming the concave and convex portions. As for the extent that the metal ring packing to be interlocked with the concave and convex portions of the protrusion portion is deformed, the metal ring packing need not be deformed so as to be interlocked with the entire thickness of the protrusion portion, that is, with the entire thickness of a flange when the protrusion portion is provided as a flange. Accordingly, the same effect as in (1) above can also be obtained in the configuration described in (2) above. An example in which the front end facing surface in the flange is provided with concave and convex portions along the circumferential direction as described in (2) above includes a shape in which the front end facing surface is raised or sunk at intervals along the circumferential direction.

(3) In a preferred embodiment, a gas sensor according to (1) or (2) above is provided, wherein: the element protection cap is replaced by an assembly of a plurality of element protection caps; the metal ring packing is disposed so as to abut a front end facing surface of a protrusion portion of one of the element protection caps located in the outermost side; and concave and convex portions are formed in the protrusion portion of the element protection cap located in an outermost side, so that the metal ring packing is deformed and thereby interlocked with the concave and convex portions when the crimping cylindrical portion is compressively deformed.

The gas sensor may have one element protection cap (of one layer) or may have an assembly of a plurality (generally, two) of element protection caps, the assembly being fixed to the metal shell. In such an assembly, ventholes in respective element protection caps are arranged so as not to overlap each other. As such, the gas to be measured, water, etc., is prevented from directly colliding with the surface of the element. Also in the case where the assembly of element protection caps is fixed to the metal shell, the same effect as in (1) above can be obtained when the concave and convex portions are provided in the protrusion portion of the element protection cap located in an outermost side. That is, each element protection cap is firmly fixed to the metal shell because the metal ring packing is deformed so as to be relatively interlocked with the concave and convex portions provided in the protrusion portion on an outer circumference of the open end of the element protection cap.

(4) In a second aspect, the invention provides a gas sensor including: a cylindrical metal shell; a detection element having a detection portion provided on a front end side thereof, the detection element being fixed inside the metal shell while the detection portion of the detection element protrudes from a front end side of the metal shell; and an element protection cap having ventholes, the element protection cap being fixed to the metal shell so that a region of the detection element protruding from the front end side of the metal shell is covered with the element protection cap; the metal shell including an annular front-end-facing end surface provided in a front end region of the metal shell so that the detection element is enclosed in the annular front-end-facing end surface, and a crimping cylindrical portion extending to the front end side on an outer circumference of the front-end-facing end surface; the element protection cap including a protrusion portion which extends outward from a rear end side of the element protection cap and is received in the crimping cylindrical portion, the protrusion portion of the element protection cap being disposed in the crimping cylindrical portion, the crimping cylindrical portion being compressively deformed toward the front-end-facing end surface while being bent inward to cover the protrusion portion so that the protrusion portion of the element protection cap is pressed against the front-end-facing end surface to thereby fix the element protection cap to the metal shell; wherein: the protrusion portion of the element protection cap includes concave and convex portions provided outward along an outer circumferential direction while a metal ring packing is disposed between the front-end-facing end surface inside the crimping cylindrical portion and a rear end facing surface of the protrusion portion of the element protection cap, so that the metal ring packing is deformed and thereby interlocked with the concave and convex portions when the crimping cylindrical portion is compressively deformed.

The embodiment described in (4) differs from the embodiment described in (1) above in that the metal ring packing is disposed between the front-end-facing end surface of the shell and the protrusion portion of the cap. Thus, the embodiment described in (4) is a modification of the embodiment described in (1) above. Also in this context the same effect described in (1) also can basically be obtained in the embodiment described in (4) above. Namely, because the metal ring packing is deformed so as to be relatively interlocked with the concave and convex portions in the protrusion portion of the element protection cap, the element protection cap is more firmly fixed to the metal shell by such deformation as compared to a background-art fixing structure using crimping incapable of deforming the metal ring packing in this manner. Moreover, because both a pressure bonding portion between the front-end-facing end surface of the shell and the metal ring packing, and a pressure bonding portion between the metal ring packing and the compressively deformed crimping cylindrical portion are provided, the regions where the convex portions among the concave and convex portions are provided are pressure-bonded so as to bear a relatively high pressure in the circumferential direction. Thus, the fixing force of the cap can be increased.

(5) Further, in a preferred embodiment, a gas sensor according to (4) above is provided, wherein: a protrusion portion of an element protection cap formed as an annular flange is provided in place of the protrusion portion of the element protection cap including the concave and convex portions provided outward along the outer circumferential direction; and a rear end facing surface of the flange is provided with concave and convex portions along a circumferential direction so that the metal ring packing is deformed and thereby interlocked with the concave and convex portions.

This configuration corresponds to the configuration described in (2) above. It is apparent from the above description that the same effect as described in (4) can also be obtained in the configuration described in (5) above.

(6) Further, in a preferred embodiment, a gas sensor according to (4) or (5) above is provided, wherein: the element protection cap is replaced by an assembly of a plurality of element protection caps; and concave and convex portions are formed in a protrusion portion of one of the element protection caps located in an innermost side while the metal ring packing is disposed between the front-end-facing end surface inside the crimping cylindrical portion and a rear end facing surface of the protrusion portion of the element protection cap located in the innermost side, so that the metal ring packing is deformed and thereby interlocked with the concave and convex portions when the crimping cylindrical portion is compressively deformed. Also in the case where the assembly of element protection caps is thus fixed to the metal shell, the same effect as described in (4) above can be obtained when the concave and convex portions are provided in the protrusion portion of the element protection cap located in an innermost side. That is, each element protection cap is firmly fixed to the metal shell. This is because the metal ring packing is deformed so as to be interlocked with the concave and convex portions provided in the protrusion portion on an outer circumference of the open end of the element protection cap.

DESCRIPTION OF REFERENCE NUMERALS

Figure 1:
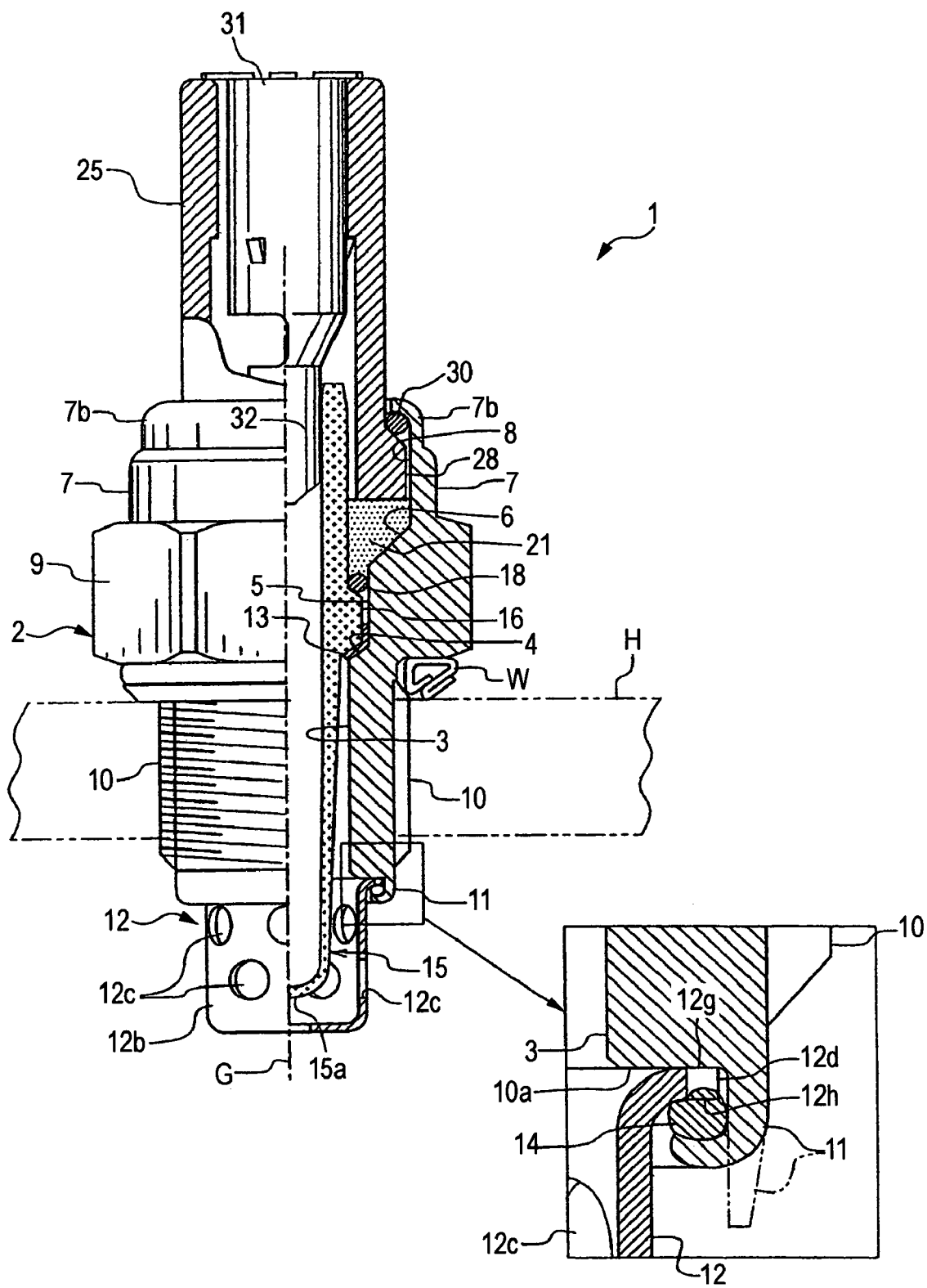
FIG. 1 is a half-sectional front view showing an embodiment of a gas sensor according to the invention, and an enlarged view showing attachment of an element protection cap to a metal shell.

Reference numerals used to identify various structural features in the drawings include the following;

1 gas sensor
2 metal shell
10a front-end-facing end surface of front end region of the metal shell
11 crimping cylindrical portion
12 element protection cap
12c venthole
12d protrusion portion of the element protection cap
12e concave portion in the protrusion portion
12f convex portion in the protrusion portion
12g rear end facing surface of the protrusion portion
12h front end facing surface of the protrusion portion
14 metal ring packing
15 detection element

DETAILED DESCRIPTION OF THE INVENTION

An example mode embodying a gas sensor according to the invention will be described in detail with reference to FIGS. 1 through 6. However, the present invention should not be construed as being limited thereto.

In the drawings, sensor 1 of this embodiment includes: a cylindrical metal shell 2 having coaxial steps such that an intermediate portion in a direction of an axis G has a large diameter; a detection element 15 in the shape of a bottomed cylinder and disposed/fixed inside the shell 2; an output terminal member 31 disposed in a cylindrical inner protection sleeve 25 provided in the rear (upper portion in FIG. 1); and an element protection cap 12 covering a detection portion on a front end 15a side (lower end side in FIG. 1) of the detection element 15 protruding from a front end side of the metal shell 2. The sensor 1 is fabricated as follows.

For example, the metal shell 2 is made of SUS430. The metal shell 2 has a small-diameter hole 3 formed so that an inner surface on the front end side (lower end side in FIG. 1) has a shape akin to a small circle in sectional view. An inner circumferential step portion 4 which is tapered with a diameter increasing upward is provided circumferentially in an upper end portion (shown in FIG. 1) of the small-diameter hole 3. A cylindrical inner circumferential surface 5 which is straight and shaped like a circle in sectional view is formed in the rear (upper portion in FIG. 1) of the inner circumferential step portion 4. A cylindrical portion 7 having an inner circumferential surface 8 with a diameter larger than the diameter of the cylindrical inner circumferential surface 5 is provided in the rear of the cylindrical inner circumferential surface 5 through a taper surface 6 with a diameter increasing in an upward direction. The rear end region of the cylindrical portion 7 is provided as a thin portion 7b. The thin portion 7b is pressed against the rear end by a die (not shown) so that the thin portion 7b is compressively deformed toward the rear end side while being bent inward from a cylindrical state coaxial with the axis G of the sensor 1. A flange 28 formed in a front end portion of the sleeve 25 is disposed inside the cylindrical portion 7. An O-ring packing 30 made of a metal wire is interposed in a rear end surface of the flange 28. When the thin portion 7b of the cylindrical portion 7 is compressively deformed, the flange 28 is pressed against the front end side to compress a seal member (such as talc powder) 21 disposed on the front end side of the flange 28. By compression of the seal member 21, the detection element 15 inserted in the metal shell 2 is fixed while sealability of the detection element 15 is ensured. The detection element 15 has an outer circumferential convex potion (flange) 16 provided in an intermediate portion of the detection element 15 in the lengthwise (axis G) direction. The outer circumferential convex potion 16 has a large diameter and is disposed along the outer circumferential surface. While the outer circumferential convex potion 16 is supported by the inner circumferential step portion 4 in the metal shell 2 through a plate packing 13, a ring packing 18 made of a metal (Ni) wire is disposed on the base end (rear end) side of the outer circumferential convex potion 16. The seal member 21, in which an annular space above the packing 18 is filled as shown in FIG. 1, is compressed. A terminal member 31 formed so as to be bent like a cylinder is inserted in the sleeve 25. A small-diameter portion (inner connection terminal) 32 which is a front end region is pressure-bonded to a reference electrode layer (not shown) on the inner surface of the element 15.

On the other hand, a hexagonal portion 9 with an extended diameter for attachment (screwing) to an exhaust pipe H forms a radially outward part of the metal shell 2 corresponding to the cylindrical inner circumferential surface 5. A male thread 10 for attachment to the exhaust pipe (screwhole) H is provided in the outer circumference of the small-diameter hole 3 in a lower portion of the hexagonal portion 9. In FIG. 1, the reference symbol W designates a washer for sealing at the time of screwing. A front-end-facing end surface 10a which is concentric (coaxial) with the male thread 10 and which is shaped annularly to form a surface perpendicular to the axis G is provided in the inside of the front end region of the male thread 10 and at a front end of the small-diameter hole 3. A crimping cylindrical portion (cylindrical portion) 11 made of a thin cylindrical portion having an outer diameter slightly smaller than the root diameter of the male thread 10 is provided in the outside of the front-end-facing end surface 10a so as to be concentric with the front-end-facing end surface 10a and the male thread 10. The element protection cap 12 is disposed inside the crimping cylindrical portion 11 and fixed through a metal ring packing 14. The fixing is achieved by crimping such that the front end region of the crimping cylindrical portion 11 is compressively deformed toward the rear end side (upper portion in FIG. 1) while being bent inward (toward the axis G). Before the compressive deformation, the crimping cylindrical portion 11 is shaped like a cylinder coaxial with the axis G as represented by the chain double-dashed line in an enlarged view of FIG. 1. Furthermore, the outer circumferential surface of the front end region of the crimping cylindrical portion 11 is tapered down.

Figure 2:
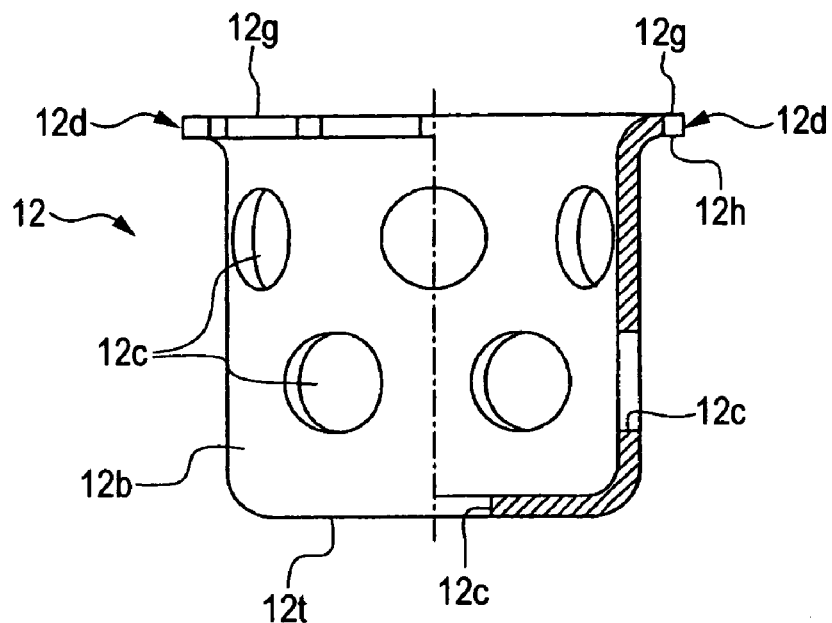
FIG. 2 is a half-sectional frontal enlarged view of an element protection cap used in the gas sensor depicted in FIG. 1.
Figure 3:
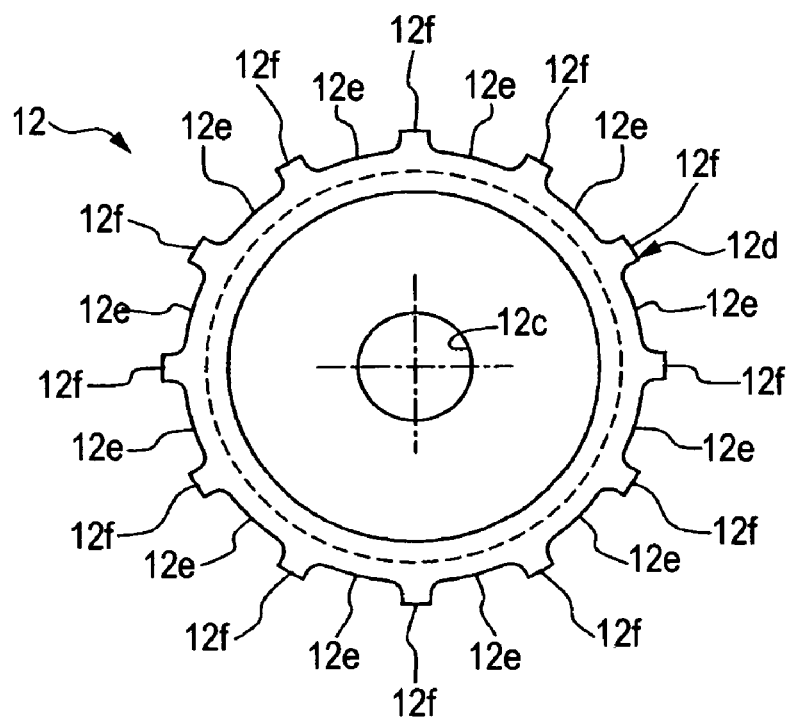
FIG. 3 is a plan view of FIG. 2.

The element protection cap 12 and fixing thereof will be described in more detail. That is, as shown in FIG. 2, the element protection cap 12 in this embodiment is shaped like a bottomed cup. The element protection cap 12 has a cylindrical portion (cylinder-shaped portion) 12b as its side portion, and a bottom portion 12t. Ventholes 12c are provided in adequate places of the cylindrical portion 12b so as to allow for good contact of exhaust gas with the detection element 15 while also protecting the detection element. A venthole 12c is provided in the center of the bottom portion 12t. An annular protrusion portion 12d protruding outward is provided on the outer circumference of an open end (upper end in FIG. 2) of the cylindrical portion 12b (see FIG. 3). In this embodiment, the protrusion portion 12d is formed concavoconvexly outward along the outer circumferential direction to thereby form outer teeth composed of concave portions 12e and convex portions 12f (see FIGS. 2 and 3). The inner diameter of the open end of the cylindrical portion 12b is set to be substantially equal to the inner diameter of the small-diameter hole 3. The maximum outer diameter of a region where the protrusion portion 12d is provided is set to be slightly smaller than the inner diameter of the crimping cylindrical portion 11. As a result, the region of the open end of the element protection cap 12 inclusive of the protrusion portion 12d is formed so as to fit into the crimping cylindrical portion 11 and abut the front-end-facing end annularly shaped surface 10a. In this embodiment, the element protection cap 12 is prepared in such manner that a plate of SUS310S is press-molded. Although FIG. 3 shows the case where each concave portion 12e has a depth equal to about a half of the protruded length of the protrusion portion 12d from the convex portion 12f, the invention is not limited thereto. For example, each concave portion 12e may have a depth equal to the entire protruded length of the protrusion portion 12d or may be further extended to the cylindrical portion 12b. In this case, the protrusion portion is formed from convex portions 12f protruding outward from the cylindrical portion 12b.

Figure 4A:
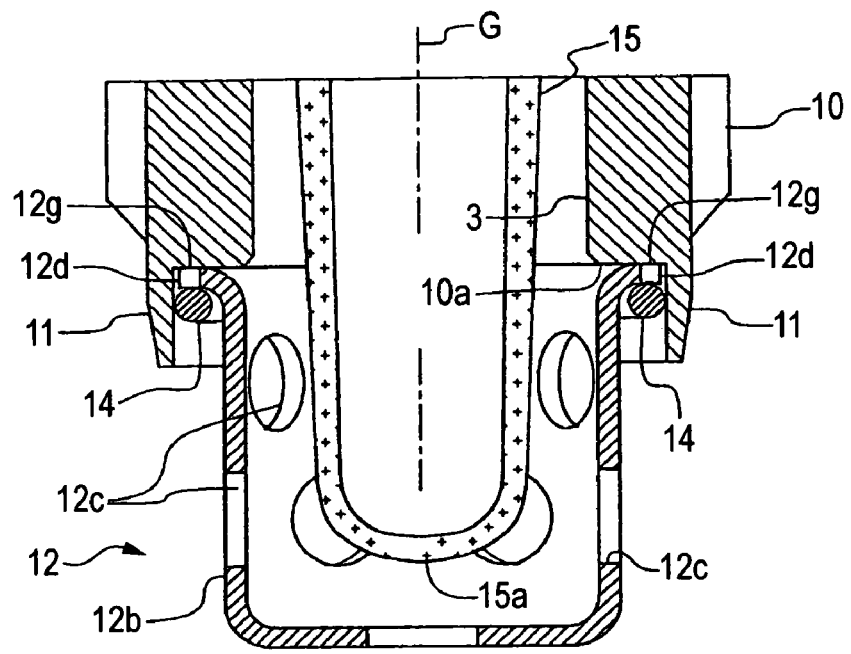
FIGS. 4A and 4B are explanatory views of a process for fixing the element protection cap in the gas sensor depicted in FIG. 1.
Figure 4A:
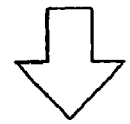
Figure 4B:
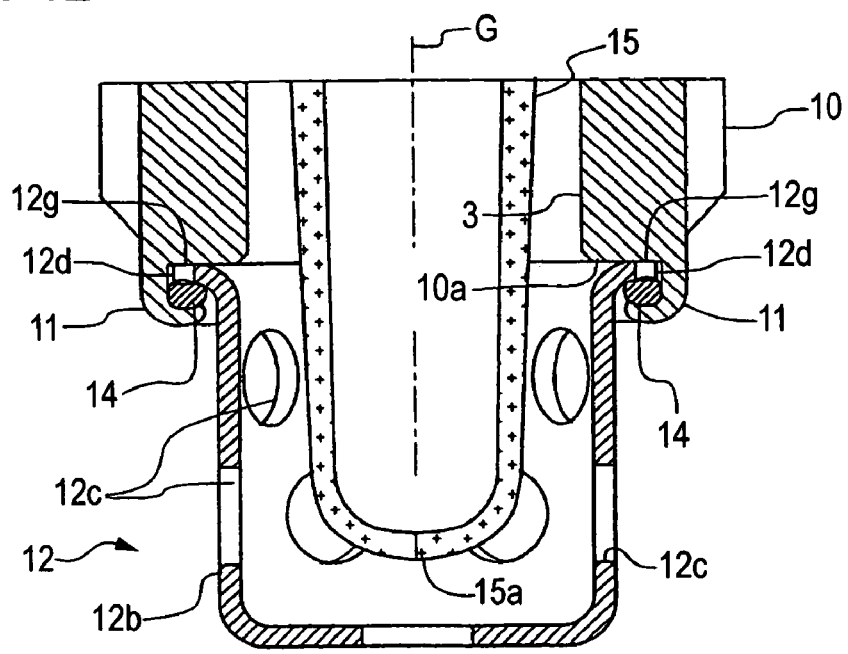
Figure 5A:
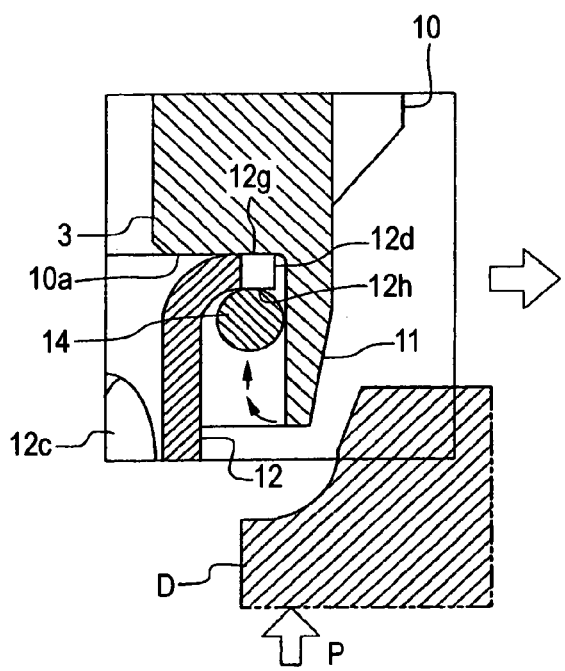
FIGS. 5A and 5B are explanatory views of a process for compressively deforming a crimping cylindrical portion of a metal shell in FIGS. 4A and 4B.
Figure 5B:
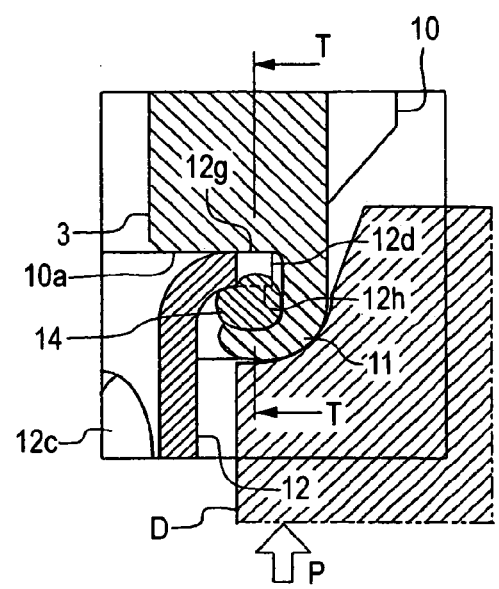

Thus, the open end of the element protection cap 12 is disposed in the crimping cylindrical portion 1I so that the region of the detection element 15 protruding from the front end side of the metal shell 2 is covered with the element protection cap 12. The element protection cap 12 is fixed to the metal shell 2 as follows (see FIGS. 4A, 4B, 5A and 5B). That is, the rear end facing surface 12g of the protrusion portion 12d on the open end side outer circumference of the element protection cap 12 is first disposed so as to abut the annular front-end-facing end surface 10a in the crimping cylindrical portion 11 (see FIGS. 4A and 5A). On this occasion, in this embodiment, the metal ring packing 14 is disposed so as to be fitted onto the cylindrical portion 12b of the element protection cap 12 and abut the front end facing surface 12h of the protrusion portion 12d (see FIGS. 4A and 5A). An end ring which is formed in such manner that a wire material of nickel, shaped like a circle in sectional view, is bent like a circular ring. The ring is used as the metal ring packing 14. In this embodiment, crimping is performed in this state so that the crimping cylindrical portion 11 is compressively deformed toward the annular front-end-facing end surface 10a while being bent inward as shown in FIGS. 4B and 5B. As shown in FIGS. 5A and 5B, the crimping cylindrical portion 11 is compressively deformed (crimped) in such manner that the front end region of the crimping cylindrical portion 11 before deformation is pressed from the cylindrical state coaxial with the axis G of the sensor 1 toward the rear end side by force P of a die D having a section as shown in FIGS. 5A and 5B. As a result, crimping is performed so that the crimping cylindrical portion 11 is compressively deformed while being bent inward (toward the axis G). The protrusion portion 12d and the metal ring packing 14 are deformed so as to be compressed between the deformed crimping cylindrical portion 11 and the annular front-end-facing end surface 10a, to thereby fix the element protection cap 12 to the metal shell 2.

Figure 6:
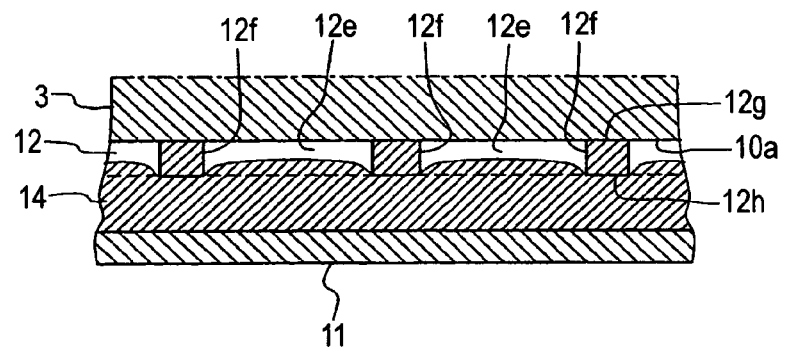
FIG. 6 is a partial expansion plan view of a section taken along the line T-T in FIG. 5B.

In such fixing, the protrusion portion 12d of the element protection cap 12 is formed with outer teeth including concave and convex portions formed outward along the outer circumferential direction (see FIG. 3). For this reason, in the compressive deformation, the metal ring packing 14 is deformed so as to be relatively interlocked with (attached to) the concave and convex portions (FIGS. 5B and 6). That is, the metal ring packing 14 is deformed so as to penetrate into the concave portions 12e between the teeth (convex portions 12f). FIG. 6 is a partial expansion plan view of a section taken along the line T-T in FIG. 5B. In this embodiment, because the force for fixing the element protection cap 12 to the metal shell 2 is increased by such interlocking deformation, the element protection cap 12 is firmly fixed to the metal shell 2. In such fixing, both a pressure bonding portion between the front-end-facing end surface 10a of the shell 2 and the rear end facing surface 12g of the protrusion portion 12d of the cap 12, and a pressure bonding portion between the metal ring packing 14 and the compressively deformed crimping cylindrical portion 11 are formed, so that the pressure borne by regions where the convex portions 12f are provided becomes relatively high in the circumferential direction. In this embodiment, it is considered that an increase in fixing force is combined with such increase in pressure borne by the convex portions 12f. Thus, when the sensor 1 having such a structure for fixing the element protection cap 12 to the metal shell 2 is put into use in a condition that sensor 1 is screwed and attached into the exhaust pipe H of the engine through the male thread 10 of the shell 2, the element protection cap 12 can be restrained from being loosened or rattled and accordingly from rotating around the axis G.

The following test was conducted in order to demonstrate the effects of the invention.

The aforementioned sensor 1 was used. The shell 2 of the sensor 1 was fixed. Rotation force around the axis G was applied to the element protection cap 12 fixed to the shell 2. Torque for starting rotation was measured. The torque was compared with torque in a background-art product which was prepared in such manner that a cap differing in that the concave and convex portions were not provided in the protrusion portion 12d was fixed. Consequently, the product according to this embodiment required a large torque for starting rotation in a range of from 200% to 250% compared with the background-art product. Namely, this result demonstrates the effect of the invention.

Figure 7:
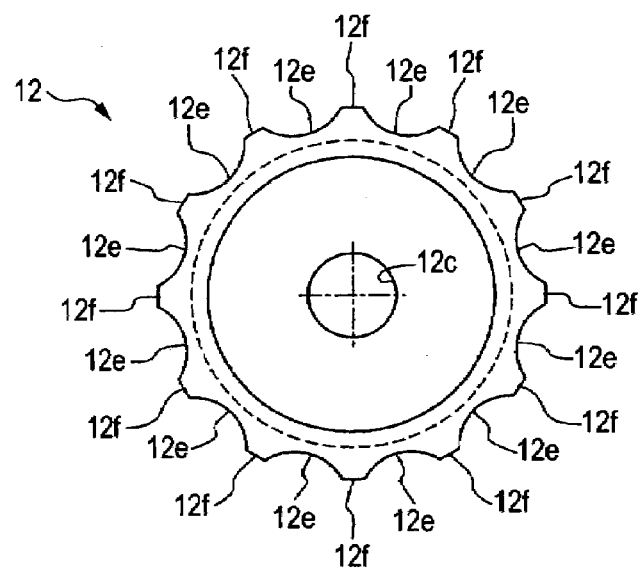
FIG. 7 is a plan view showing another example of concave and convex portions provided in a protrusion portion of the element protection cap.

Although the above embodiment illustrates the case where the protrusion portion 12d of the element protection cap 12 has convex portions 12f shaped like outer teeth and disposed at regular angular intervals as viewed from the direction of the axis G, the convex portions 12f may be provided at irregular angular intervals. The convex portions 12f need not be rectangular as shown in FIG. 3. As represented by an element protection cap 12 in FIG. 7, the concave portions 12e may be shaped like circular arcs with respect to the convex portions 12f or the convex portions may be shaped like circular arcs conversely.

Figure 8:
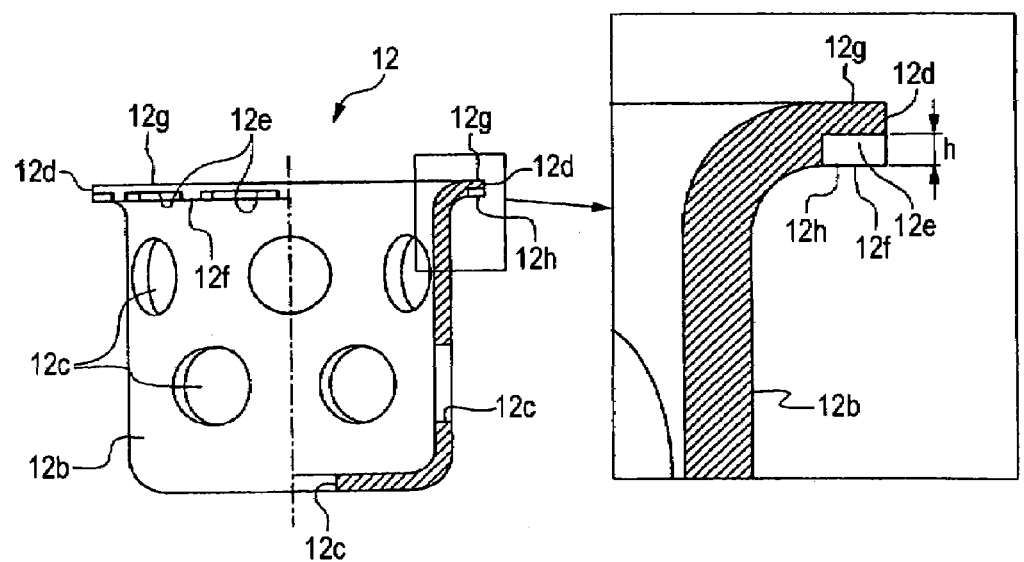
FIG. 8 is a half-sectional frontal enlarged view showing an element protection cap used in an embodiment of a gas sensor according to a preferred embodiment described in (2) above, and an enlarged view of a part of the element protection cap.
Figure 9:
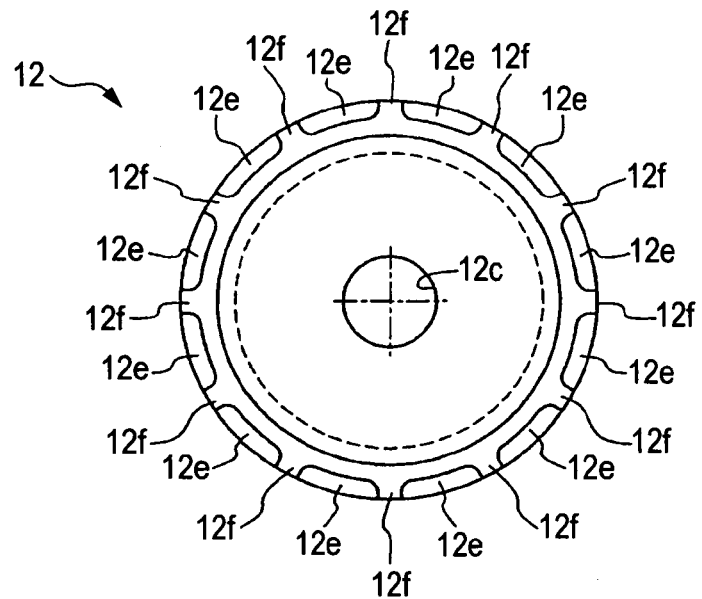
FIG. 9 is a bottom view of FIG. 8.
Figure 10:
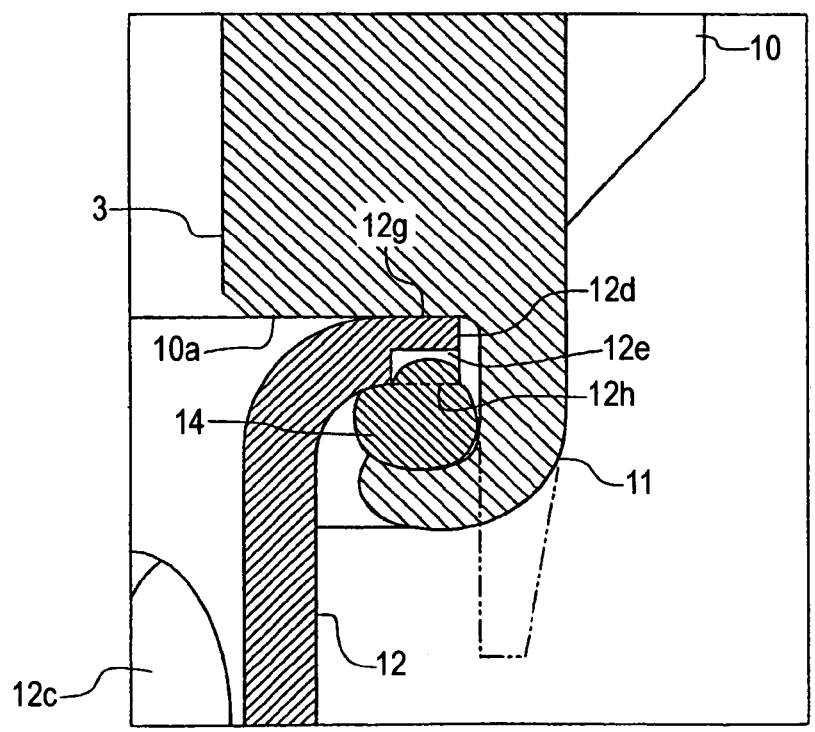
FIG. 10 is an enlarged sectional view of a part of a gas sensor according to a preferred embodiment described in (2) above using the element protection cap depicted in FIGS. 8 and 9.

An embodiment according to (2) above will be described below with reference to FIGS. 8 through 10. In this embodiment, the protrusion portion 12d provided as an annular flange protruding outward and having a front end facing surface (lower surface in FIG. 8) provided concavoconvexly (concave portions 12e and convex portions 12f) along the circumferential direction is used instead of the protrusion portion 12d of the element protection cap 12 provided outward concavoconvexly along the outer circumferential direction in the aforementioned embodiment). This embodiment differs in that the metal ring packing 14 is deformed so as to be interlocked with the concave and convex portions as shown in FIG. 10. Accordingly, points of difference will be described while like numerals refer to like parts. This rule applies to the following embodiments.

That is, in this embodiment, the protrusion portion 12d of the element protection cap 12 is provided as an annular flange and concave portions 12e each having a predetermined depth h (e.g., half of the thickness of the plate forming the element protection cap) are provided at intervals of a predetermined circumferential pitch in a front end facing surface 12h of the protrusion portion 12d so that the protrusion portion 12d is provided with concave and convex portions (concave portions 12e and convex portions 120 along the circumferential direction. Also in this embodiment, because the metal ring packing 14 is deformed so as to be relatively interlocked with the concave and convex portions (concave portions 12e and convex portions 12f), the same effect as in the aforementioned embodiment can be obtained. That is, in the embodiment shown in FIG. 1, the metal ring packing 14 is interlocked with the concave and convex portions in the protrusion portion 12*d* of the element protection cap 12 without use of the entire thickness of the protrusion portion 12*d*. Also, in the element protection cap 12 according to this embodiment in which the concave portions 12*e* each having a predetermined depth h are suitably placed in the front end facing surface 12*h* of the protrusion portion 124, the same effect as in the embodiment shown in FIG. 1 can be obtained.

Figure 11:
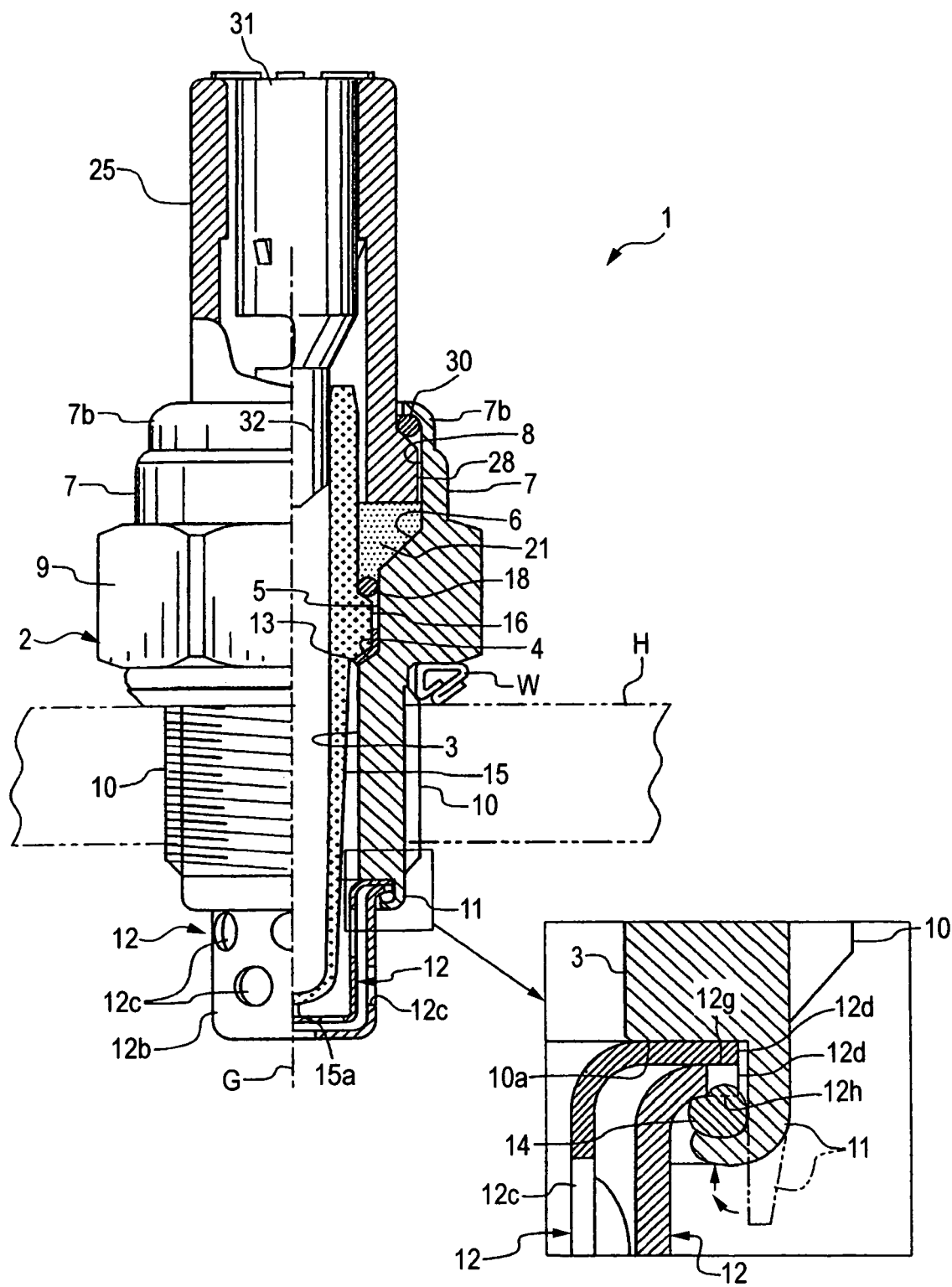
FIG. 11 is a half-sectional front view of a gas sensor according to a preferred embodiment described in (3) above, and an enlarged view showing attachment of inner and outer protection caps to the metal shell.

An embodiment of the invention according to (3) above will be described below with reference to FIG. 11. In this embodiment, the element protection cap in the embodiment shown in FIG. 1 is replaced by an assembly of inner and outer element protection caps 12 so that the metal ring packing 14 abuts on the front end facing surface 12*h* of the protrusion portion 12*d* of the outer element protection cap 12. That is, because two element protection caps 12 are provided so that the small inner element protection cap 12 and the large outer element protection cap 12 overlap each other, this embodiment differs from the embodiment shown in FIG. 1 in that the small element protection cap 12 is interposed between the front-end-facing end surface 10*a* of the shell 2 and the element protection cap 12 in the embodiment shown in FIG. 1. Accordingly, points of difference will be described while like numerals refer to like parts.

In this embodiment, the inner element protection cap 12 is shown as a slightly thinner cap. The outer diameter of the protrusion portion (flange) 12*d* on the outer circumference of the rear end as an open end of the inner element protection cap 12 is set to be equal to the outer diameter of the protrusion portion (flange) 12*d* on the outer circumference of the rear end as an open end of the outer element protection cap 12. The protrusion portion 12*d* of the inner element protection cap 12 is provided as an annular flange. This embodiment differs from the embodiment shown in FIG. 1 in that the protrusion portion (flange) 12*d* of the inner element protection cap 12 is clamped between the front-end-facing end surface 10*a* of the shell 2 and the protrusion portion 12*d* of the element protection cap 12. Thus, in the case where the invention is embodied by such an assembly of element protection caps 12, increased fixing force can be attained as compared with an assembly structure having only a single protection cap. In this embodiment, ventholes 12*c* in the inner and outer caps are disposed so as not to overlap each other. For this reason, the gas to be measured is prevented from directly colliding with the detection portion of the element 15. Also in the case where a cap shown in FIGS. 8 and 9 is used as the outer element protection cap in FIG. 11, the same effect can be obtained.

An embodiment of the invention according to (4) above will be described below with reference to FIG. 12. In this embodiment, the metal ring packing 14 of the embodiment shown in FIG. 1 is disposed between the annular front-end-facing end surface 10*a* and the rear end facing surface 12*g* of the protrusion portion 12*d* of the element protection cap 12 inside the crimping cylindrical portion 11. In this state, the crimping cylindrical portion 11 is compressively deformed toward the front-end-facing end surface 10*a* while being bent inward. That is, this embodiment differs from the embodiment shown in FIG. 1 in the position where the metal ring packing 14 is disposed. The operation and effect due to compressive deformation of the metal ring packing 14 is substantially the same in terms of the structure for fixing the element protection cap 12. Like numerals refer to like parts and detailed description thereof will be omitted here.

Figure 12:
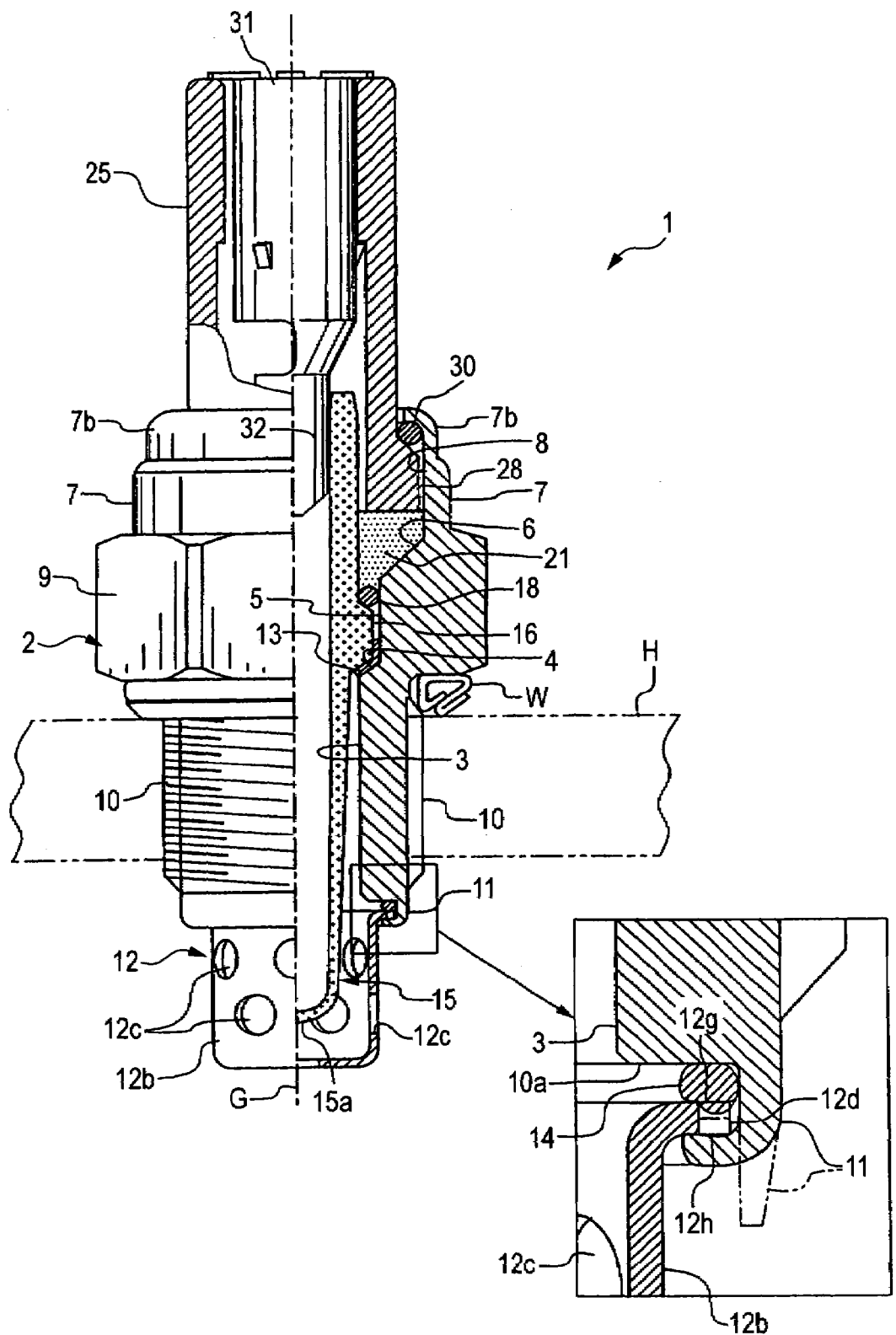
FIG. 12 is a half-sectional front view of a gas sensor according to a preferred embodiment described in (4) above, and an enlarged view showing attachment of the protection cap to the metal shell.
Figure 13:
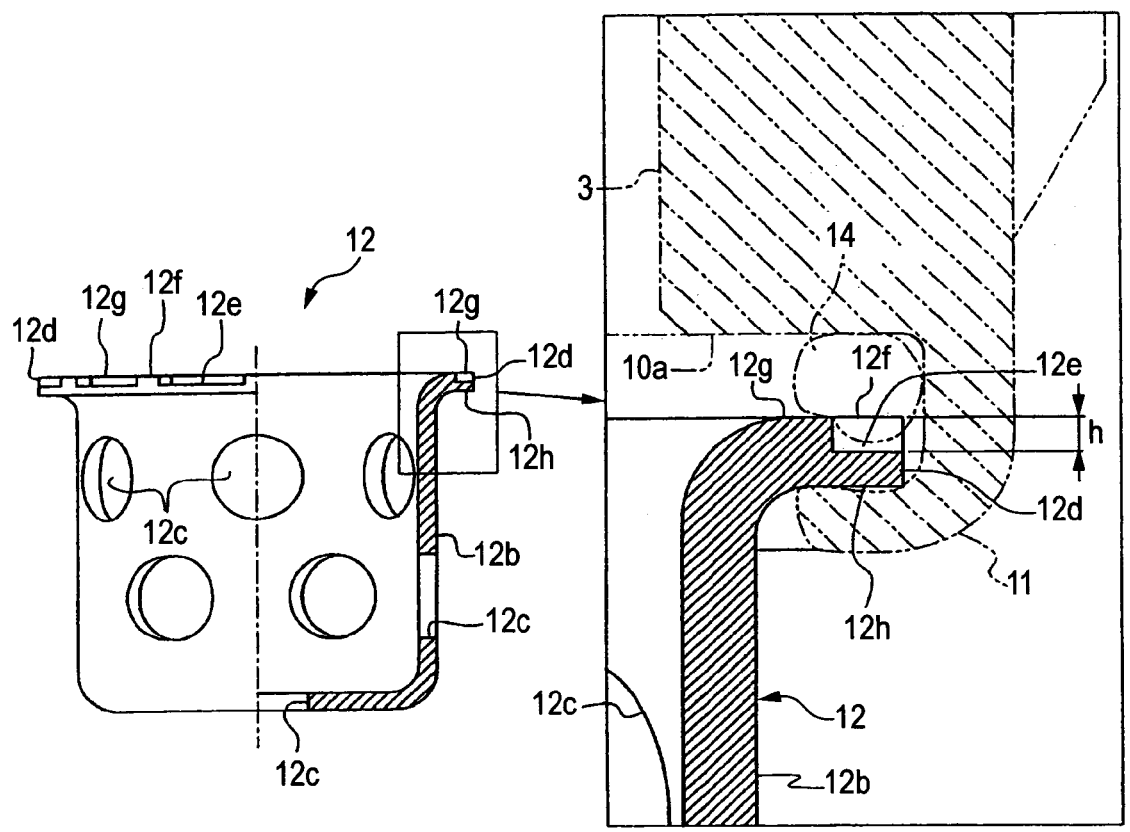
FIG. 13 is a half-sectional frontal enlarged view showing an element protection cap used in a gas sensor according to a preferred embodiment described in (5) above, and an enlarged view showing attachment of the element protection cap to the metal shell.
Figure 14:
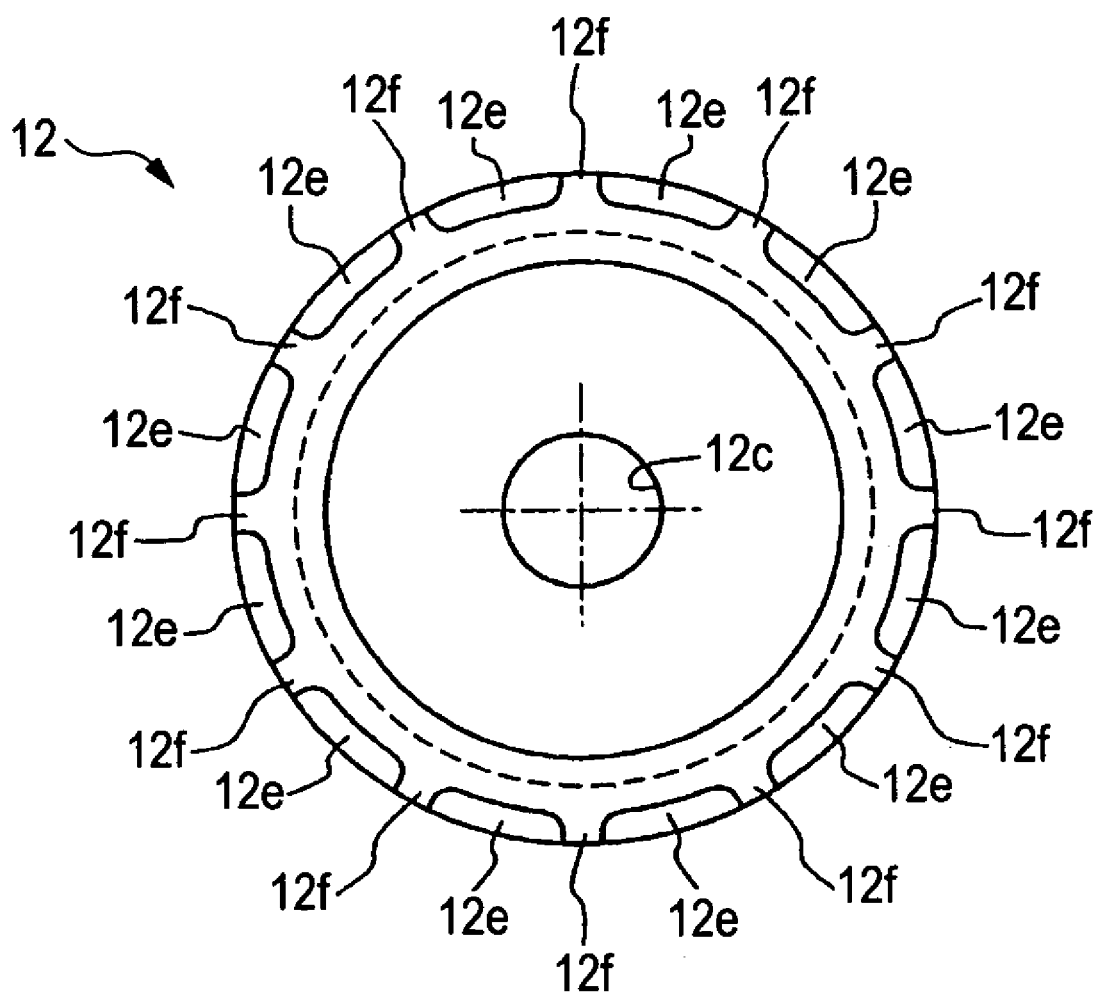
FIG. 14 is a plan view of FIG. 13.

When an element protection cap 12 shown in FIGS. 13 and 14 is used in the embodiment shown in FIG. 12, an embodiment according to (5) above is provided. That is, while the protrusion portion 12*d* of the element protection cap 12 is not shaped like outer teeth but shaped like an annular flange with a predetermined thickness, the rear end facing surface (upper surface in FIG. 13) of the flange is provided concavoconvexly (concave portions 12*e* and convex portions 12*f*) along the circumferential direction as shown in FIGS. 13 and 14. That is, it is apparent from the enlarged view of FIG. 13 that substantially same effect as the embodiment shown in FIG. 12 can be obtained when such an element protection cap 12 is used.

Figure 15:
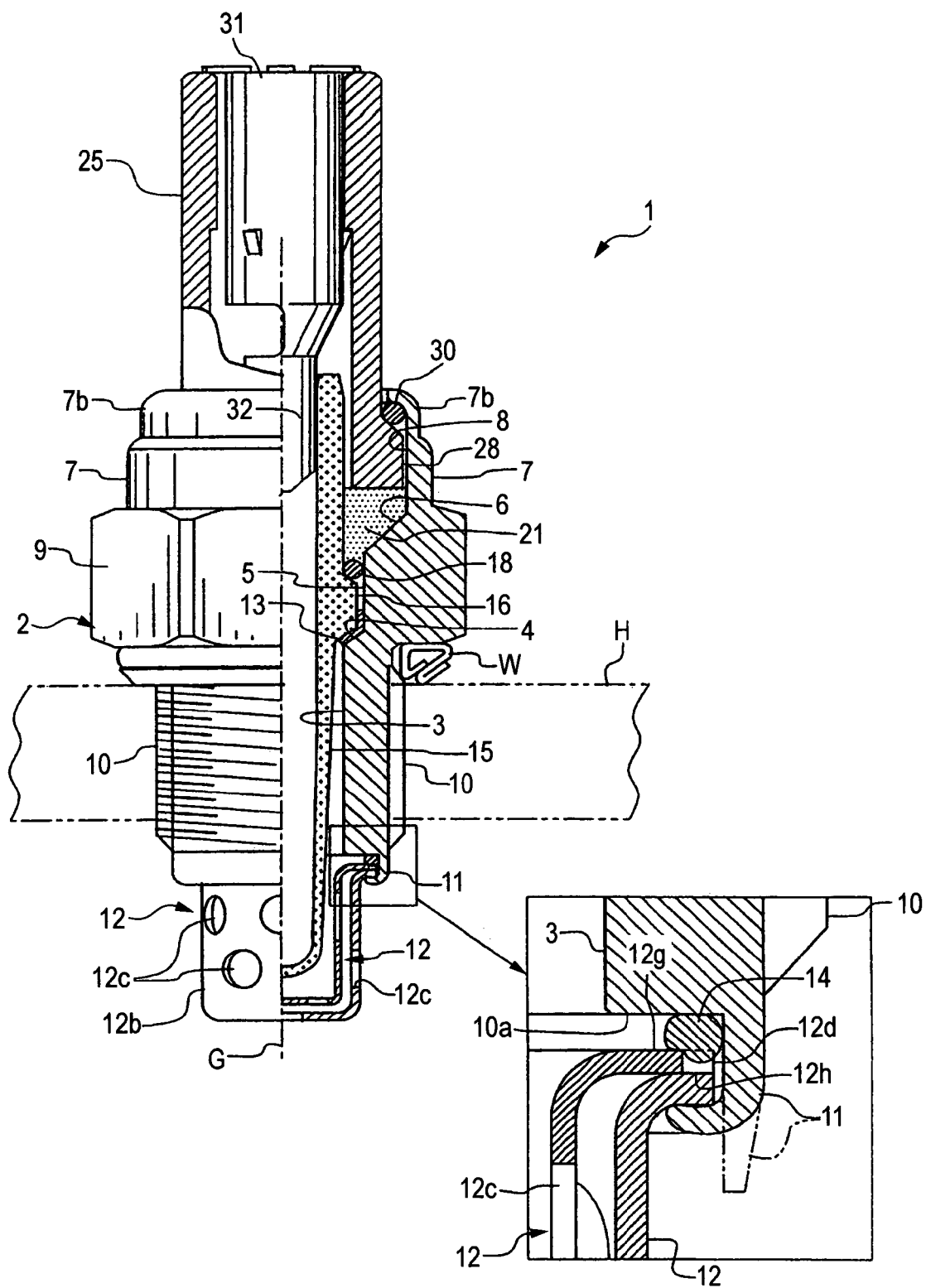
FIG. 15 is a half-sectional front view of a gas sensor according to a preferred embodiment described in (6) above, and an enlarged view showing attachment of inner and outer protection caps to the metal shell.

FIG. 15 shows an embodiment according to (6) above. In this embodiment, the element protection cap of the embodiment shown in FIG. 12 is replaced by an assembly of inner and outer element protection caps 12. Concave and convex portions are provided in the protrusion portion 12*d* of the inner element protection cap 12 so that the metal ring packing 14 abuts the rear end facing surface 12*g* of the protrusion portion 12*d*. The protrusion portion 12*d* of the outer element protection cap 12 is provided as an annular flange. In the condition such that the protrusion portion 12*d* provided as the flange is disposed between the concavoconvexly provided protrusion portion 12*d* and the crimping cylindrical portion 11, the crimping cylindrical portion 11 is compressively deformed. That is, two element protection caps 12 are provided so that the inner smaller-diameter cap 17 and the outer larger diameter cap 12 overlap each other. This embodiment differs from the embodiment show in FIG. 12 in that another element protection cap 12 not having concave and convex portions is interposed between the element protection cap 12 and the crimping cylindrical portion 11. In this embodiment, the inner element protection cap 12 is shown as a slightly thinner cap. Thus, also in such a structure where the element protection caps 12 overlap each other, increased fixing force can be attained. Also in the case where an element protection cap as shown in FIGS. 13 and 14 is used as the inner element protection cap in FIG. 15, the same effect can be obtained.

The invention is not limited to the aforementioned embodiments and may be embodied while various design changes are made. For example, when the protrusion portion of the element protection cap is shaped like outer teeth provided outward concavoconvexly along the outer circumferential direction, each of the teeth need not be rectangular in view from the direction of the axis as described above. Any suitable shape may be used as the shape of the protrusion portion of the element protection cap. For example, the protrusion portion of the element protection cap may be shaped like a wavy portion made of a repetition of concave or convex circular arcs along the circumferential direction. Although the case has been described where concave and convex portions for forming the protrusion portion are provided in the outside of the outer diameter of the cylindrical portion, the convex portions may be provided so as to extend from the outer circumferential surface of the cylindrical portion. In this case, each concave portion between adjacent convex portions becomes large in radial size (amount of protrusion) in view from the direction of the axis, so that the interlocking characteristic of the metal ring packing is improved. Moreover, when convex portions are provided, the convex portions may be provided at regular angular intervals or may be provided at irregular angular intervals. In any case, an increase in fixing force can be obtained when the metal ring packing is deformed so as to be relatively interlocked with the concave and convex portions.

Also in the case where the protrusion portion of the element protection cap is provided as an annular flange while the front end facing surface or rear end facing surface of the flange is provided with concave and convex portions along the circumferential direction, the concave and convex portions need not be rectangular in view from the direction of the axis. Particularly, the protrusion portions may be such that the metal ring packing is deformed so as to be relatively interlocked with the concave and convex portions. The depth h of each concave portion in this case may be set in consideration of the state in which the metal ring packing is relatively interlocked with the concave and convex portions. In addition, the invention can be applied to an assembly of protection caps. The number of element protection caps is not limited to two.

Although the case has been described where the invention is embodied by use of a cylindrical cap as the element protection cap, the invention can likewise be embodied by use of a semispherical or dome-shaped cap as the element protection cap. Although the case has been described where an end ring is used as the metal ring packing, the invention can be applied to the case where an endless ring is used as the metal ring packing. Although the case has been described where the metal ring packing is shaped to have a circular sectional view before deformation, design of the metal ring packing shape can be changed suitably. Although the case has been described where the metal ring packing is made of nickel, the invention is not limited thereto. Furthermore, as described above, the metal ring packing is preferably made of a metal having a hardness that is lower than that of the material of the metal shell or the element protection cap.

Although the case has been described where the invention is embodied by use of a bottomed cup-shaped oxygen sensor as the detection element, the shape of the detection element in the invention is not limited thereto. For example, as a matter of course the invention can be embodied by use of a sensor prepared by fixing a plate-like or rod-like detection element. In addition, the invention can be embodied by use of various kinds of gas sensors other than the oxygen sensor.

This application is based on Japanese Patent application JP 2004-282467, filed Sep. 28, 2004, the entire content of which is hereby incorporated by reference, the same as if set forth at length.

What is claimed is:

1. A gas sensor comprising:
a cylindrical metal shell;
a detection element having a detection portion provided on a front end side thereof, the detection element being fixed inside the metal shell while the detection portion of the detection element protrudes from a front end side of the metal shell; and
an element protection cap having ventholes, the element protection cap being fixed to the metal shell so that the detection portion of the detection element is covered with the element protection cap,
the metal shell including an annular front-end-facing end surface provided in a front end region of the metal shell, and a crimping cylindrical portion extending to the front end side on an outer circumference of the front-end-facing end surface,
the element protection cap including a protrusion portion which extends outward from a rear end side of the element protection cap and is received in the crimping cylindrical portion, the protrusion portion of the element protection cap being disposed in the crimping cylindrical portion while a metal ring packing is disposed so as to abut a front end facing surface of the protrusion portion, the crimping cylindrical portion being compressively deformed toward the front-end-facing end surface while being bent inward to cover the metal ring packing so that the protrusion portion of the element protection cap is pressed against the front-end-facing end surface through the metal ring packing thereby fixing the element protection cap to the metal shell, wherein:
the protrusion portion of the element protection cap on which the metal ring packing abuts includes concave and convex portions provided outward along an outer circumferential direction, so that the metal ring packing is deformed and thereby interlocked with the concave and convex portions when the crimping cylindrical portion is compressively deformed; and
the metal ring packing has a hardness lower than that of the element protection cap.

2. A gas sensor comprising:
a cylindrical metal shell;
a detection element having a detection portion provided on a front end side thereof, the detection element being fixed inside the metal shell while the detection portion of the detection element protrudes from a front end side of the metal shell; and
an element protection cap having ventholes, the element protection cap being fixed to the metal shell so that the detection portion of the detection element is covered with the element protection cap,
the metal shell including an annular front-end-facing end surface provided in a front end region of the metal shell, and a crimping cylindrical portion extending to the front end side on an outer circumference of the front-end-facing end surface,
the element protection cap including a protrusion portion which extends outward from a rear end side of the element protection cap and is received in the crimping cylindrical portion, the protrusion portion of the element protection cap being disposed in the crimping cylindrical portion while a metal ring packing is disposed so as to abut a front end facing surface of the protrusion portion, the crimping cylindrical portion being compressively deformed toward the front-end-facing end surface while being bent inward to cover the metal ring packing so that the protrusion portion of the element protection cap is pressed against the front-end-facing end surface through the metal ring packing thereby fixing the element protection cap to the metal shell, wherein:
the protrusion portion of an element protection cap is formed as an annular flange;
a front end facing surface of the flange includes concave and convex portions provided along a circumferential direction so that the metal ring packing is deformed and thereby interlocked with the concave and convex portions; and
the metal ring packing has a hardness lower than that of the element protection cap.

3. A gas sensor comprising:
a cylindrical metal shell;
a detection element having a detection portion provided on a front end side thereof, the detection element being fixed inside the metal shell while the detection portion of the detection element protrudes from a front end side of the metal shell; and
an element protection cap having ventholes, the element protection cap being fixed to the metal shell so that the detection portion of the detection element is covered with the element protection cap,
the metal shell including an annular front-end-facing end surface provided in a front end region of the metal shell, and a crimping cylindrical portion extending to the front end side on an outer circumference of the front-end-facing end surface, the element protection cap including a protrusion portion which extends outward from a rear end side of the element protection cap and is received in the crimping cylindrical portion, the protrusion portion of the element protection cap being disposed in the crimping cylindrical portion while a metal ring packing is disposed so as to abut a front end facing surface of the protrusion portion, the crimping cylindrical portion being compressively deformed toward the front-end-facing end surface while being bent inward to cover the metal ring packing so that the protrusion portion of the element protection cap is pressed against the front-end-facing end surface through the metal ring packing thereby fixing the element protection cap to the metal shell, wherein:

the element protection cap comprises an assembly of a plurality of element protection caps;

the metal ring packing is disposed so as to abut a front end facing surface of a protrusion portion of one of the element protection caps located in an outermost side;

concave and convex portions are formed in the protrusion portion of the element protection cap located in the outermost side, so that the metal ring packing is deformed and thereby interlocked with the concave and convex portions when the crimping cylindrical portion is compressively deformed; and the metal ring packing has a hardness lower than that of the element protection cap.

4. A gas sensor comprising:

a cylindrical metal shell;

a detection element having a detection portion provided on a front end side thereof, the detection element being fixed inside the metal shell while the detection portion of the detection element protrudes from a front end side of the metal shell; and an element protection cap having ventholes, the element protection cap being fixed to the metal shell so that a region of the detection element protruding from the front end side of the metal shell is covered with the element protection cap, the metal shell including an annular front-end-facing end surface provided in a front end region of the metal shell so that the detection element is enclosed in the annular front-end-facing end surface, and a crimping cylindrical portion extending to the front end side on an outer circumference of the front-end-facing end surface, the element protection cap including a protrusion portion which extends outward from a rear end side of the element protection cap and is received in the crimping cylindrical portion, the protrusion portion of the element protection cap being disposed in the crimping cylindrical portion, the crimping cylindrical portion being compressively deformed toward the front-end-facing end surface while being bent inward to cover the protrusion portion so that the protrusion portion of the element protection cap is pressed against the front-end-facing end surface to thereby fix the element protection cap to the metal shell, wherein:

the protrusion portion of the element protection cap includes concave and convex portions provided outward along an outer circumferential direction while a metal ring packing is disposed between the front-end-facing end surface inside the crimping cylindrical portion and a rear end facing surface of the protrusion portion of the element protection cap, so that the metal ring packing is deformed and thereby interlocked with the concave and convex portions when the crimping cylindrical portion is compressively deformed; and the metal ring packing has a hardness lower than that of the element protection cap.

5. A gas sensor comprising:

a cylindrical metal shell;

a detection element having a detection portion provided on a front end side thereof, the detection element being fixed inside the metal shell while the detection portion of the detection element protrudes from a front end side of the metal shell; and an element protection cap having ventholes, the element protection cap being fixed to the metal shell so that a region of the detection element protruding from the front end side of the metal shell is covered with the element protection cap, the metal shell including an annular front-end-facing end surface provided in a front end region of the metal shell so that the detection element is enclosed in the annular front-end-facing end surface, and a crimping cylindrical portion extending to the front end side on an outer circumference of the front-end-facing end surface, the element protection cap including a protrusion portion which extends outward from a rear end side of the element protection cap and is received in the crimping cylindrical portion, the protrusion portion of the element protection cap being disposed in the crimping cylindrical portion while a metal ring packing is disposed between the front-end-facing end surface inside the crimping cylindrical portion and a rear end facing surface of the protrusion portion of the element protection cap, the crimping cylindrical portion being compressively deformed toward the front-end-facing end surface while being bent inward to cover the protrusion portion so that the protrusion portion of the element protection cap is pressed against the front-end-facing end surface to thereby fix the element protection cap to the metal shell, wherein:

the protrusion portion of the element protection cap is formed as an annular flange;

a rear end facing surface of the flange is provided with concave and convex portions along a circumferential direction so that the metal ring packing is deformed and thereby interlocked with the concave and convex portions; and the metal ring packing has a hardness lower than that of the element protection cap.

6. A gas sensor comprising:

a cylindrical metal shell;

a detection element having a detection portion provided on a front end side thereof, the detection element being fixed inside the metal shell while the detection portion of the detection element protrudes from a front end side of the metal shell; and an element protection cap having ventholes, the element protection cap being fixed to the metal shell so that a region of the detection element protruding from the front end side of the metal shell is covered with the element protection cap, the metal shell including an annular front-end-facing end surface provided in a front end region of the metal shell so that the detection element is enclosed in the annular front-end-facing end surface, and a crimping cylindrical portion extending to the front end side on an outer circumference of the front-end-facing end surface, the element protection cap including a protrusion portion which extends outward from a rear end side of the element protection cap and is received in the crimping cylindrical portion, the protrusion portion of the element protection cap being disposed in the crimping cylindrical portion, the crimping cylindrical portion being compressively deformed toward the front-end-facing end surface while being bent inward to cover the protrusion portion so that the protrusion portion of the element protection cap is pressed against the front-end-facing end surface to thereby fix the element protection cap to the metal shell, wherein:

the element protection cap comprises an assembly of a plurality of element protection caps;

concave and convex portions are formed in a protrusion portion of one of the element protection caps located in an innermost side while a metal ring packing is disposed between the front-end-facing end surface inside the crimping cylindrical portion and a rear end facing surface of the protrusion portion of the element protection cap located in the innermost side, so that the metal ring packing is deformed and thereby interlocked with the concave and convex portions when the crimping cylindrical portion is compressively deformed; and the metal ring packing has a hardness lower than that of the element protection cap.

7. A gas sensor comprising:

a detection element including a detection portion in a front end side;

an element protection cap including ventholes, and a protrusion portion including concave and convex portions protruding outward in a rear end side, the element protection cap covering the detection portion; and a cylindrical metal shell including a fixing portion provided in a front end side thereof for crimping the protrusion portion, the cylindrical metal shell enclosing the detection element, wherein the protrusion portion is crimped to the cylindrical metal shell through a metal ring packing interlocked with the concave and convex portions; and the metal ring packing has a hardness lower than that of the element protection cap.

8. The gas sensor as claimed in claim 7, wherein the concave and convex portions are formed outward along an outer circumferential direction of the protrusion portion.

9. The gas sensor as claimed in claim 7, wherein the protrusion portion is formed as an annular flange having a front end facing surface provided with said concave and convex portions.

10. The gas sensor as claimed in claim 7, wherein the protrusion portion is formed as an annular flange having a rear end facing surface provided with said concave and convex portions.

* * * * *